United States Patent [19]

Marx et al.

[11] 4,075,337
[45] Feb. 21, 1978

[54] METHODS OF COMBATTING BACTERIAL INFECTIONS IN WARM-BLOODED ANIMAL WITH CEPHALSPORIN R-SULFOXIDE

[75] Inventors: Arthur Friedrich Marx, Delft; Jan Verwey, Leiden; Peter Max Smid, Bleiswijk, all of Netherlands

[73] Assignee: Gist-Brocades N.V., Delft, Netherlands

[21] Appl. No.: 633,006

[22] Filed: Nov. 18, 1975

Related U.S. Application Data

[62] Division of Ser. No. 377,934, July 10, 1973, abandoned.

[30] Foreign Application Priority Data

July 18, 1972 United Kingdom .................33596/72
Oct. 23, 1972 United Kingdom .................48720/72

[51] Int. Cl.² ...................... A61K 31/54; A61K 31/43
[52] U.S. Cl. ...................................... 424/246; 424/271
[58] Field of Search .......................................... 424/246

[56] References Cited

U.S. PATENT DOCUMENTS 3,641,014  2/1972  Murphy et al. ...................... 424/246

Primary Examiner—Jerome D. Goldberg
Attorney, Agent, or Firm—Hammond & Littell

[57] ABSTRACT

R-sulfoxides of the formulae

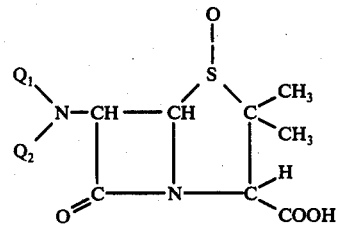

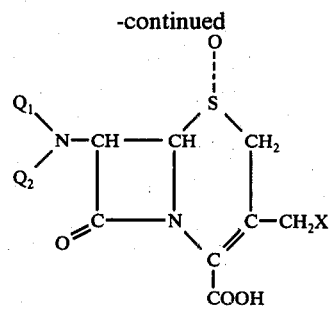

and

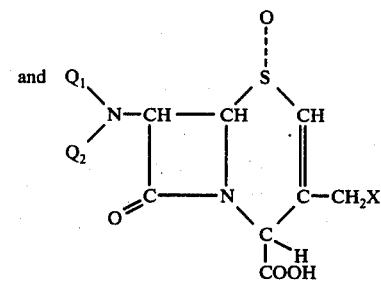

wherein

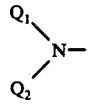

represents an usual penicillin or cephalosporin amide group and X is selected from the group consisting of hydrogen, hydroxy, an alkanoyloxy and the residue of a nucleophilic agent and their salts and esters are prepared by oxidation of the corresponding penicillins and cephalosporins to convert the sulfur atom in the ring to a sulfoxide group and separating and isolating the penicillin- or cephalosporin R-sulfoxide so formed from the reaction mixture or by acylation of the free amino group of the intermediate 6-aminopenicillanic acid R-sulfoxide and 7-aminocephalosporanic acid R-sulfoxide and derivatives. A preferred straight oxidation method is the photosensitized oxygenation method.

2 Claims, No Drawings

METHODS OF COMBATTING BACTERIAL INFECTIONS IN WARM-BLOODED ANIMAL WITH CEPHALSPORIN R-SULFOXIDE

STATE OF THE ART

This is a division of Ser. No. 377,934, filed July 10, 1973, now abandoned.

During the last decade, sulfoxides of 6-amino-penicillanic acid derivatives and 7-amino-cephalosporanic acid derivatives including 7-amino-desacetoxycephalosporanic acid derivatives have been prepared chiefly as intermediates in the preparation of cephalosporins useful in the therapeutic applications as antibiotics. Preparation of these sulfoxides has generally involved oxidation of derivatives of 6-amino-penicillanic acid and 7-amino-cephalosporanic and 7-amino-desacetoxycephalosporanic acids with organic peracids or sodium periodate. Such oxidations are generally performed on esters or amides of the aforesaid acids and usually provide chiefly or exclusively the corresponding sulfoxides having the S-configuration. The resulting S-sulfoxides in general possess only a low degree of antibacterial activity against Gram-positive bacteria or practically none at all. The corresponding S-sulfoxides of the free penicillanic acids and cephalosporanic acids, obtained by removal of the protecting ester or amide group on the S-sulfoxides after the oxidation or by direct oxidation of the free acids, possess antibacterial properties but insuifficient to make them of real interest as therapeutics.

Other previously known methods which may be used for the oxidation of the ring sulfur atom in penicillanic acid derivatives or in dihydrocephalosporanic acid derivatives involve the use of ozone or phenyliodosodichloride, and these methods produce mixtures of sulfoxides having the S-configuration and the R-configuration [see, for example, D. O. Spry, J. Org. Chem., 37, 793 (1972), and J. Amer. Chem. Soc., 92, 5006 (1970)]. Such mixtures of S- and R-penicillin and cephalosporin sulfoxides have not been of commercial interest as antibacterial agents.

OBJECTS OF THE INVENTION

It is an object of the invention to provide novel R-sulfoxides of penicillin and cephalosporin derivatives, free from association with the S-sulfoxides of such penicillin or cephalosporin compounds.

It is another object of the invention to provide a novel process for the preparation of the said R-sulfoxides.

It is a further object of the invention to provide novel antibacterial compositions and to a novel method of combatting bacterial infections in warm-blooded animals.

These and other objects and advantages of the invention will become obvious from the following detailed description.

THE INVENTION

The novel products of the invention are the R-sulfoxides of 6-amino-penicillanic acid compounds and the R-sulfoxides of 7-amino-cephalosporanic acid and its derivatives free from the S-sulfoxides of such penicillin or cephalosporin compounds. The compounds of the invention are penicillin and cephalosporin sulfoxides having the R-configuration of the formulae

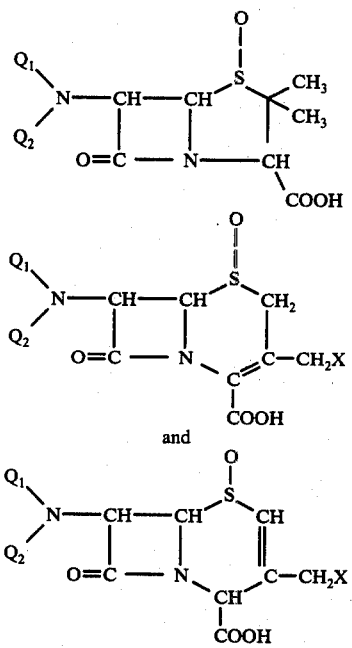

wherein X is selected from the group consisting of hydrogen, hydroxy, an alkanoyloxy group (preferably acetoxy) and the residue of a nucleophilic agent and

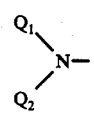

represents a usual penicillin or cephalosporin amide group and salts and esters of such acids.

By the term "residue of a nucleophilic agent" are meant residues such as halogen, azido, cyano, carbamoyloxy, an optionally substituted heterocyclic containing a sulfur or nitrogen atom such as pyridinyl, —S—A wherein A is selected from the group consisting of a diazolyl, triazolyl, tetrazolyl, thiazolyl, thiadiazolyl, thiatriazolyl, oxazolyl, isoxazolyl, oxadiazolyl, benzimidazolyl, benzoxazolyl, triazolopyridinyl and purinyl, —CH$_2$—COOZ$_1$ wherein Z$_1$ is lower alkyl,

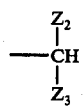

in which Z$_2$ and Z$_3$ are the same or different and each is selected from the group consisting of hydrogen, lower alkyl, an aryl optionally substituted with lower alkyl, cycloalkyl of 5 or 6 carbon atoms, lower alkoxycarbonyl, arylcarbonyl or diaryl-carbonyl connected to lower alkoxy, lower alkanoyl, aryloxycarbonyl and cyano,

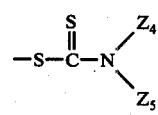

wherein Z$_4$ lower alkyl and Z$_5$ is selected from the group consisting of lower alkyl and cycloalkyl of 5 to 6 carbon atoms, or $Z_4$ and $Z_5$ together with the nitrogen atom to which they are attached is selected from the group consisting of pyrrolidino, piperidino and morpholino,

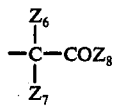

wherein $Z_6$ and $Z_7$ are the same or different and each is selected from the group consisting of hydrogen, lower alkyl, phenyl, substituted phenyl, lower alkoxycarbonyl, mono- or di-aryl(lower)alkoxycarbonyl, lower alkylcarbonyl, aryl(lower)alkyl and cycloalkyl of 5 to 6 carbon atoms, and $Z_8$ is selected from the group consisting of hydrogen, lower alkyl, phenyl, substituted phenyl, aryl(lower)alkyl and cycloalkyl of 5 to 6 carbon atoms,

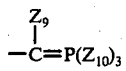

wherein the groups $Z_{10}$ are the same or different and each is selected from the group consisting of lower alkyl, phenyl, cycloalkyl group of 5 to 6 carbon atoms and di(lower)alkyl amino, and $Z_9$ is selected from the group consisting of hydrogen and an ester, acyl, nitro and cyano.

The term "lower" as applied herein to alkyl, alkanoyl and alkoxy groups means that the group in question contains at most four carbon atoms.

By the term "a usual penicillin or cephalosporin amide group" are meant those groups known in relation to penicillins and cephalosporins or analogues thereof, wherein e.g. $Q_1$ is hydrogen or a group linked to the nitrogen atom by a carbon or sulfur atom, $Q_2$ is hydrogen or lower alkyl or phenyl(lower)alkyl, or $Q_1$ and $Q_2$, together with the nitrogen atom to which they are attached, collectively represent a heterocyclic group, e.g. a succinimido, phthalimido, oxazolidinyl or imidazolidinyl which may carry one or more substitutents.

The group represented by $Q_1$ in formulae I to III may be any group hitherto disclosed in relation to penicillins and cephalosporins or analogues thereof. Thus $Q_1$ can represent, for example, an alkanoyl group containing up to 20 carbon atoms, a phenyl(lower)alkanoyl, phenoxy(lower)alkanoyl, phenyl(lower)alkyloxycarbonyl, (lower)-alkanoylaminocarbonyl, (lower)alkoxy(lower)alkanoyl, salicyl optionally substituted by one or two halogen atoms, phenoxyphenyl(lower)alkanoyl, isoxazolyl(lower)alkanoyl, isoxazolylcarbonyl, benzoyl, naphthoyl, formyl, oxazolidinyl,phenyl-α-amino(lower)alkanoyl, thienyl- or furyl(lower)-alkanoyl, thienyl- or furyl-α-amino-(lower)alkanoyl, phenylthio(lower)alkanoyl, 2-benzofuranyl(lower)alkanoyl, benzenesulfonyl, 1-piperidinosulfonyl, p-tolylsulfinyl, cyclohexylsulfinyl, benzylsulfinyl, benzenesulfinyl or naphthalenesulfinyl group. The phenyl and heterocyclyl radicals of such groups may carry substituents such as halogen atoms, lower alkyl, carboxy, phenyl-(lower)alkoxy, tri(lower)alkylphenyl, di(halo)phenyl, amino, nitro, cyano, trifluoromethyl and methylthio groups.

The symbol $Q_2$ may represent, for example, hydrogen, methyl, ethyl, isobutyl, or benzyl group. Moreover, the symbols $Q_1$ and $Q_2$ together with the nitrogen atom to which they are attached may represent an optionally substituted heterocyclic group such as phthalimido, succinimido, saccharinyl or imidazolidinyl. Suitable groups represented by the grouping

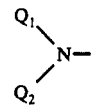

in formulae I, II and III are benzyloxycarbamoyl, phenylacetamido, phenoxyacetamido, 3-acetyl-ureido, (3,5-dichlorosalicyl)amino, 2-phenoxy-propionamido, 2-phenoxybutyramido, 2-phenoxyphenylacetamido, 5-methyl-3-phenyl-4-isoxazolecarboxamido, 5-methyl-3-(o-chlorophenyl)-4-isoxazolecarboxamido, 5-methyl-3-(2,6-dichlorophenyl)-4-isoxazolecarboxamido, 3-(2,6-dichlorophenyl)-5-isoxazolyl-acetamido, 3-methyl-5-isoxazolyl-acetamido, 3-(2,4,6-trimethylphenyl)-5-isoxazolyl-acetamido, 5-methyl-3-(2-chloro-6-fluorophenyl)-4-isoxazolecarboxamido, 2,6-dimethoxy-benzamido, 2-ethoxy-1-naphthamido, 2-(o-aminobenzamido)-phenyl-acetamido-N-methyl, 2-(2-amino-5-nitrobenzamido)-phenylacetamido-N-methyl, N-benzylformamido, N-methyl-2-phenoxyacetamido, N-methyl-2-phenylacetamido, N-ethyl-2-phenylacetamido, N-isobutyl-2-phenoxyacetamido, 2-benzylidene-4,5-dioxo-3-oxazolidinyl, 2-butylsuccinimido, 2,2-dimethyl-5-oxo-4-phenyl-1-imidazolidinyl, phthalimido, saccharinyl, succinimido, α-amino-α-(1-cyclohexa-1,4-dienyl)-acetamido, α-amino-phenylacetamido, α-amino-2-thienylacetamido, 2-thienyl-acetamido, 3-thienylacetamido, 2-furylacetamido, 4-chlorophenylacetamido, 3-bromophenylacetamido, 3-nitrophenylacetamido, benzenesulfinamido, (2-ethoxynaphthyl) sulfinamido, benzylsulfinamido, cyclohexylsulfinamido, p-tolylsulfinamido, 4-nitrophenylacetamido, 3-trifluoromethylphenylacetamido, 4-cyanophenylacetamido, 4-methylthiophenylacetamido, 3-chlorophenyl-thioacetamido, 2-benzofuranylacetamido, benzenesulfonamido, benzenesulfonylaminoacetamido, p-bromo-benzenesulfonamido and 1-piperidinosulfonamido.

The compounds of formulae I, II and III, and especially the compounds of formulae I and II, possess therapeutically useful antibacterial properties.

According to the results, as obtained by in vitro bioassays, the compounds of formulae I and II are, in general, much more active than the corresponding S-sulfoxide compounds, especially against some members of the gram-negative microorganisms. Moreover, in several instances it has been found that they are also considerably more active than the corresponding non-oxygenated cephalosporins.

In some instances, an over-all improvement of activity towards gram-positive and gram-negative bacteria has been found for the R-sulfoxide. For example 7-[3-(2,6-dichlorophenyl)-isoxazol-5-yl-acetamido]-desacetoxycephalosporanic acid R-sulfoxide shows about a ten-fold increase in activity with reference to the corresponding desacetoxycephalosporin.

The penicillanic and cephalosporanic acid derivatives of formulae I, II and III have antibiotic properties which make them useful for therapeutic application to human beings and animals, alone or mixed with other known antibiotics. Some of the compounds of formulae I and II have activities comparable with those of known β-lactam antibiotics and they have particularly outstanding activities against gram-positive microorganisms such as *Bacillus subtilis*, *Staphylococcus aureus*, *Streptococcus haemolyticus* and *faecalis*, and *Diplococcus pneumoniae*. They have, moreover, a good activity against penicillin-resistant strains of Staphylococci, and this is especially so with the compounds of formula II wherein the group

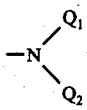

represents phenylacetamido, 2-thienylacetamido, 3-(2,6-dichlorophenyl)-isoxazol-5-yl-acetamido, 3-methyl-isoxazol-5-yl-acetamido, α-amino-phenylacetamido and X is hydrogen or acetoxy, and salts of such compounds. They are also active against gram-negative microorganisms such as *Pasteurella multocida* and *Klebsiella pneumoniae*.

The R-sulfoxide compounds of the invention are preferably employed for therapeutic purposes in the form of a non-toxic, pharmaceutically acceptable salt such as the sodium, potassium or calcium salt. Other salts that may be used include the non-toxic, suitably crystalline salts with organic bases such as amines, for example trialkylamines, procaine and dibenzylamine.

In the treatment of bacterial infections, the compounds of this invention can be administered topically, orally or parenterally, in accordance with conventional procedures for administration of antibiotics. They are administered in dosage units containing an effective amount of the active ingredient in combination with suitable physiologically-acceptable carriers or excipients. The usual daily dose is 5 to 100 mg/kg depending upon the specific compound and the method of use.

In order to make the compounds of the formulae I, II and III more suitable for absorption in the body after oral administration while their antibiotic activity is maintained, it may be necessary to prepare special esters of the compounds of formulae I, II and III.

Preferred ester groups are, for instance, those of the types:

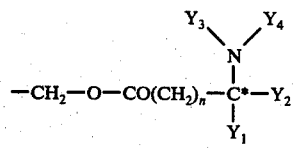
(a)

wherein the asterisk indicates the possibility of an asymetric carbon atom, $n$ is zero or an integer from 1 to 5, $Y_2$ is selected from the group consisting of hydrogen, aliphatic, aromatic, heterocyclic and aliphatic substituted with aromatic, $Y_1$, $Y_3$ and $Y_4$ each is selected from the group consisting of hydrogen and lower alkyl and, $Y_2$ and $Y_1$ together with the carbon atom to which they are attached form a 5-, 6- or 7-membered carbocyclic ring, and either $Y_3$ and $Y_4$, or $Y_4$ and $Y_1$ together with the nitrogen atom may form a heterocyclic ring, and salts of this ester group.

(b) —$CH_2$—O—CO—W, wherein W represents an optionally substituted straight- or branched-chain alkyl, (c) —$CH_2$—O—CO—$(CH_2)_n$—U, wherein $n$ is as hereinbefore defined and U is selected from the group consisting of optionally substituted aliphatic of 1 to 6 carbon atoms, cycloaliphatic having 3 to 10 carbon atoms in the ring, mono-and dicyclicaromatic and heterocyclic having 5 to 10 atoms in the ring.

The dosage units can be in the form of liquid preparations such as solutions, suspensions, dispersions or emulsions, or in a solid form such as powders, tablets and capsules.

Accordingly, the invention includes within its scope pharmaceutical compositions comprising an effective amount of a compound of formulae I, II or III, or a non-toxic, physiologically acceptable salt or ester thereof, in association with a pharmaceutically acceptable carrier or excipient. Such pharmaceutical compositions can also include one or more therapeutically active ingredients in addition to a compound of the invention. The term "effective amount" as used herein in relation to the described compounds means an amount which is sufficient to destroy or inhibit the growth of susceptible microorganisms when administered in the usual manner, in other words an amount which is sufficient to control the growth of bacteria. The magnitude of an effective amount can be easily determined by those skilled in the art through standard procedures for determining the relative activity of antibacterial agents when utilized against susceptible microorganisms via the various available routes of administration.

Suitable carriers and excipients may be any convenient physiologically acceptable ingredient which serves to facilitate administration of the therapeutically active compound. Carriers may provide some ancillary function such as that of a diluent, flavor masking agent, binding agent, action delaying agent or stabilizer. Examples of carriers include water, which can contain gelatin, acacia, alginate, dextran, polyvinylpyrrolidone or sodium carboxymethylcellulose, aqueous ethanol, syrup, isotonic saline, isotonic glucose, starch, lactose, or any other such material commonly used in pharmaceutical and veterinary antibacterial compositions.

Another aspect of the invention includes a method for inhibiting the growth of bacteria by applying to the habitat of the bacteria an effective amount of the antibacterial compounds of the invention. For example, the method can be applied to the treatment of bacterial infections in animals by administering to the host an effective amount of an antibacterial compound of the invention.

The novel compounds of the invention may also be used as growth promotors for ruminant animals such as cattle. They are also useful in in vitro applications, such as for desinfecting compositions (e.g. dairy barns) at a concentration of about 0.1 to 1% by weight of such compositions dissolved or suspended in a suitable inert carrier for application by washing or spraying.

According to a feature of the invention, R-sulfoxides of penicillanic acid and R-sulfoxides of cephalosporanic acid and its derivatives, i.e., those of formulae I, II and III, are obtained by the process which comprises the oxidation by methods known per se of the corresponding penicillins or cephalosporins to convert the sulfur atom in the ring to a sulfoxide group, and separating and isolating from the reaction mixture the penicillin or cephalosporin R-sulfoxide so formed.

As a result of research and experimentation to find a means for the oxidation of the sulfur atom of penicillanic acid and cephalosporanic acid derivatives which gives exclusively or almost so sulfoxides having the R-configuration, it has been found that oxidation methods described in the literature involving the generation of singlet oxygen ($'O_2$) generally give mixtures of R- and S-sulfoxides in which the R-isomer predominates. Thus, in the aforesaid process it is preferred to use an oxidation method involving singlet oxygen. A preferred method is the photosensitized oxygenation method wherein a solution of a cephalosporin starting material and a very small amount of a sensitizer in a suitable organic solvent through which air or oxygen is passed continuously, is irradiated with light at conveniently low temperatures (e.g. $-30°$ to $-10°$ C) to yield a mixture of R- and S-sulfoxides, and the R-sulfoxide is separated from the reaction mixture.

As suitable sensitizers may be used methylene blue, eosine, fluorescein rhodamine B and mixtures thereof. In all described experiments a 1000 Watt light source, type Philips PF 800 R was used. Methanol was used as preferred solvent.

Other known means whereby singlet oxygen may be produced in order to oxidize the sulfur atom of the penicillins and cephalosporins and may give considerable if not predominant amounts of R-sulfoxides involve, for example, the reactions depicted schematically below:

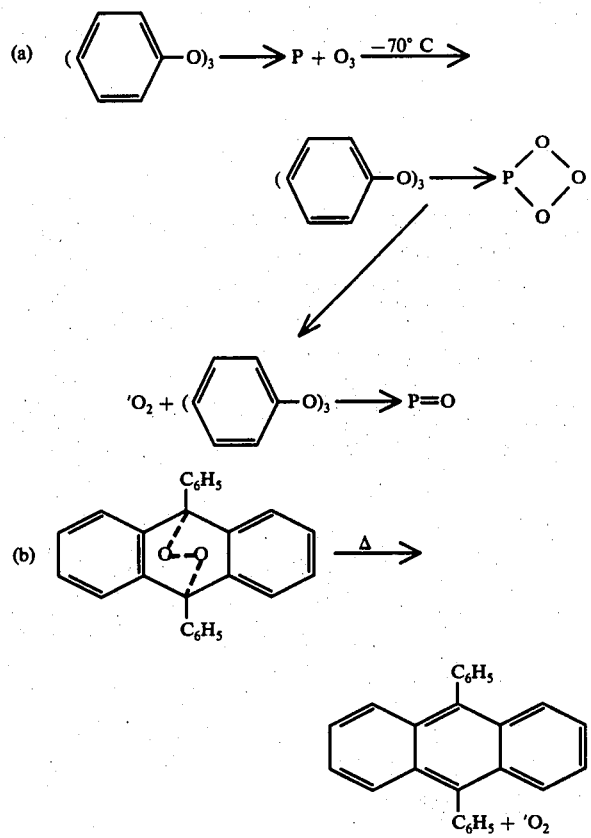

(c) $^\ominus OOH + Br_2 \longrightarrow HBr + Br^\ominus + {}'O_2$ (d) $H_2O_2 + NaOCl \longrightarrow H_2O + NaCl + {}'O_2$ (e) Ozone (hv)

Another method for the preparation of R-sulfoxides of the formulae I, II and III in relatively high yields comprises reacting the corresponding starting cephalosporanic acid derivatives or penicillanic acid derivatives with N,N'-dichlorourethane in a suitably selected organic solvent such as tetrahydrofuran, N,N-dimethylformamide and N,N-dimethylacetamide (see Tetrahedron Letters, 1972, p. 3241, M. Ochiai et al).

Preferred sulfoxides of formulae II and III may also be prepared by the oxidation of 3-acetoxy-3-methyl-cepham-4-carboxylic acid derivatives (as obtained from the reaction of a penicillin sulfoxide in refluxing acetic anhydride) into 3-acetoxy-3-methyl-cepham-4-carboxylic acid R-sulfoxides, followed by the conversion of the obtained product into desacetoxycephalosporanic acid R-sulfoxides, (for example, using triethylamine) and removal of a protecting ester group from the product so obtained (see D. O. Spry, J. Org. Chem. Vol. 37, No. 5 (1972) p. 794).

It will be appreciated that the preparation of the R-sulfoxides according to the present invention will not be restricted to the above-mentioned methods, which normally give mixtures of sulfoxides of the R-configuration and of those having the S-configuration. As a special and preferred feature of the invention, 7-substituted amino-$\Delta^3$-cephalosporanic acid sulfoxides, possessing the R-configuration, are prepared in a pure or almost pure state and accordingly isolated by means of the photosensitized oxygenation method.

According to this oxygenation method, reaction mixtures are obtained, wherein the ratio between the desired cephalosporin R-sulfoxide and the corresponding cephalosporin S-sulfoxide is within the range of 80–20% up to 95–5%.

It will be appreciated that in the unoxidized penicillin or cephalosporin starting materials corresponding to formulae I, II and III a number of functional atoms or groups of atoms may be present which are liable to be attacked during oxidation to the sulfoxide products. However, methods involving singlet oxygen, in particular as illustrated by the photosensitized oxidation method, offer very good possibilities of obtaining the novel R-sulfoxides of penicillins and especially cephalosporins containing vulnerable groups, such as a carbon-carbon double bond and a reactive —S— group etc., without the need for protection of such vulnerable groups, or of the same type or other types of groups in the grouping

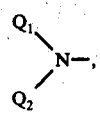

wherein $Q_1$ and $Q_2$ being as hereinbefore defined, with the possible exception of extremely sensitive groups such as primary amino or secondary amino groups.

It will be appreciated that preferred R-sulfoxide compounds of formulae I, II and III having an especially preferred side chain

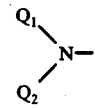

may be prepared by deacylation in manner known per se of initially prepared R-sulfoxides of formulae I, II or III not having such a side-chain, followed by an acylation process which introduces the especially preferred side-chain.

In another feature of the invention, it has been found as a result of research and experimentation that R-sulfoxides of 7-amino-cephalosporanic acid and its derivatives and of 6-amino-penicillanic acid can be prepared in practically pure state by oxidation of compounds of the formulae

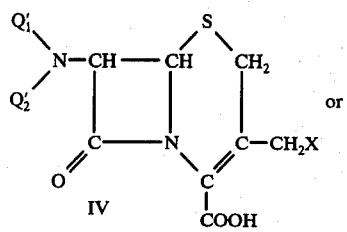

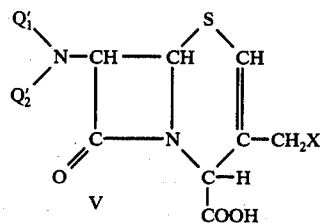

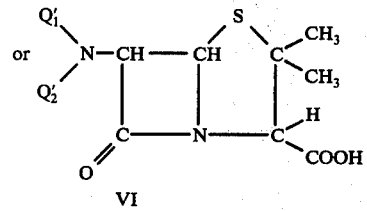

wherein X has the same significance as above and wherein $Q_1'$ and $Q_2'$, together with the nitrogen atom to which they are attached, are composing a protected amino group which can easily be replaced by a free amino group after the oxidation by methods known per se, on the condition that each $Q_1'$ and $Q_2'$ cannot represent a hydrogen atom, in an inert organic solvent, preferably separating the resulting R-sulphoxide from the reaction mixture and followed by replacing the group $$Q_1'\!\!\diagdown\!\!N\!\!-\!\!\diagup\!\!Q_2'$$

by a free amino group by methods known per se.

As preferred protected groups, which can easily be replaced after the reaction, optionally substituted arylideneamino groups such as salicylideneamino, benzylideneamino, p-hydroxybenzylideneamino, o-hydroxy-naphthylmethylideneamino, naphthylmethylideneamino, p-nitro-benzylideneamino, halohydroxybenzylideneamino, halobenzylideneamino, carbo(lower)-alkoxy-benzylideneamino (e.g. p-carbomethoxybenzylideneamino, o-carboethoxybenzylideneamino, p-carbohexyloxybenzylideneamino and m-carbobutoxybenzylideneamino), (lower)alkoxybenzylidene imino (e.g. o-methoxybenzylideneamino, p-methoxybenzylideneamino, m-methoxybenzylideneamino, p-ethoxybenzylideneamino, o-n-propoxy-benzylideneamino and p-n-hexyloxybenzylideneamino), di(lower alkyl) aminobenzylideneamino (e.g. p-dimethylaminobenzylideneamino, o-diethylaminobenzylideneamino, p-(N-n-butyl-N-methylamino)benzylideneamino and m-di-n-pentylaminobenzylideneamino, and optionally substituted alkylideneamino groups such as ethylideneamino, n-butylideneamino, isopentylideneamino, octylideneamino, heptylideneamino, 2-ethylhexylideneamino, nonylideneamino, optionally substituted by halogen hydroxy, nitro or alkoxy maybe used.

The most preferred protected groups, which may be used during the reaction in this feature of the invention, are salicylideneamino, p-nitrobenzylideneamino and p-hydroxybenzylideneamino.

The intermediate R-sulfoxides of the formulae

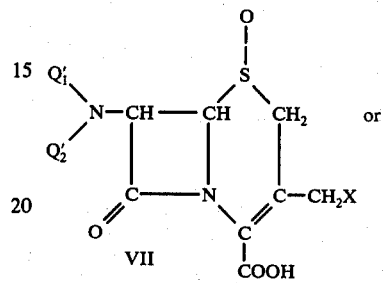

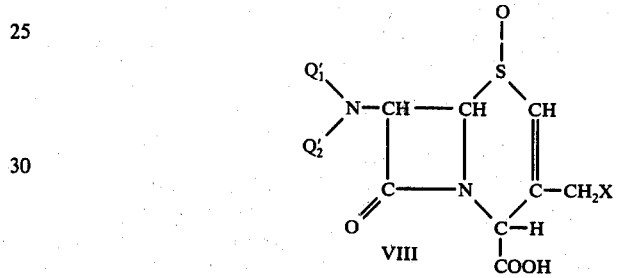

are novel compounds and form another feature of the invention while the intermediate compounds of the formula

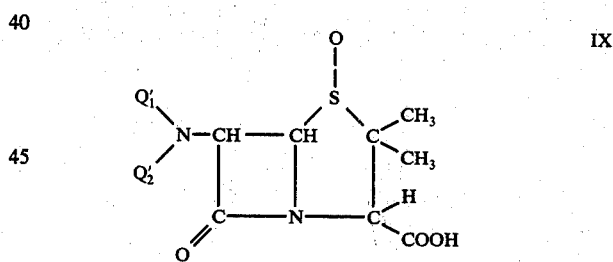

are known per se.

The desired R-sulfoxides of formulae VII, VIII and IX can be prepared by the oxidation methods known in the art and preferably by oxidation by means of optionally substituted perbenzoic acids. The yield of the R-sulfoxides of formulae VII, VIII and IX appeared to be strongly dependent on the type of the inert organic solvent wherein the oxidation was performed. For instance, the best results could be obtained in tetrahydrofuran and dioxane as compared with those which were obtained in acetonitrile, acetone and methylene chloride. The oxidation reaction is preferably carried out under anhydrous conditions and at temperatures of $-15°$ C up to $15°$ C.

In the compounds of the formulae VII, VIII and IX, the protected groups

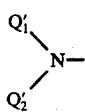

can easily be replaced by a free amino group by hydrolysis, optionally under acid conditions such as in the presence of hydrochloric acid, sulfuric acid, formic acid, oxalic acid, β-toluenesulfonic acid, trifluoroacetic acid, or acetic acid. The resulting final compounds, which are obtained in this way are those of the formulae

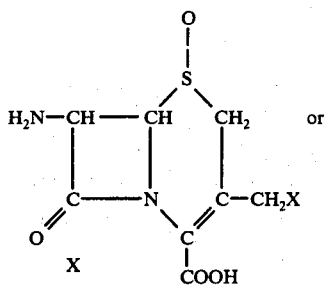

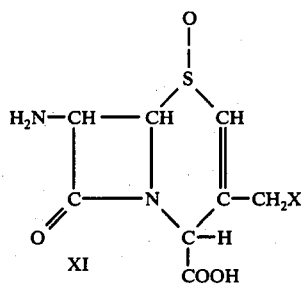

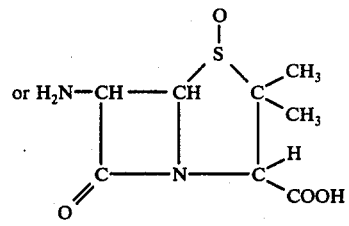

These compounds of the formulae X, XI and XII may be acylated by methods known per se giving the preferred penicillin R-sulfoxides and cephalosporin-R-sulfoxides of formulae I, II and III.

The separation and isolation of the desired R-sulfoxides from the reaction mixtures proceed by routes known per se, i.e. the mixture of the prepared S-sulfoxide and R-sulfoxide is isolated by for instance selective precipitation or extraction, followed by evaporation in vacuum, acidification and adding a salt forming agent with the necessary steps depending on the character of the solvent which was used as reaction medium. Separation of the R-sulfoxide from the isolated mixture may be performed by column chromatography using e.g. silica, acetone/acetic acid or ethylacetate/acetic acid mixtures and countercurrent extraction.

It will be appreciated that also compounds of the formulae IV, V and VI wherein the symbol

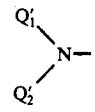

is an optionally substituted heterocyclic group such as phthalimido, succinimido, saccharinyl, 2,2-dimethyl-5-oxo-4-phenyl-1-imidazolidinyl may be oxidized to the corresponding sulfoxides of formulae VII, VIII and IX wherein the group

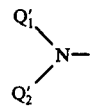

is finally desired.

It will be appreciated that the finally desired cephalosporin R-sulfoxides may also be obtained from prepared intermediate cephalosporin R-sulfoxides, containing a less desired radical X, by conversion by methods known per se of this radical X into a more preferred group.

In the following examples there are described several preferred embodiments to illustrate the invention. However, it should be understood that the invention is not intended to be limited to the specific embodiments.

EXAMPLE 1

Preparation of 7-phenylacetamido-$\Delta^3$-desacetoxycephalosporanic acid R-sulfoxide and its methyl ester 180 mg (0.5 mmole) of methylene blue were added to a solution of 5 g (15 mmoles) of 7-phenylacetamido-$\Delta^3$-desacetoxycephalosporanic acid in 1 liter of menthanol and the mixture obtained was irradiated at $-28°$ C with a 1000 W lamp for 22 hours while air was passed through. The mixture was then evaporated to dryness and the residue was chromatographed on a column (29 cm in length, 8 cm in diameter) filled with 500 g of silica gel. The eluent was a 95:5 (v/v) mixture of acetone and acetic acid.

Fractions 1 to 70 (10 ml per fraction) contained inter alia starting material and some 7-phenylacetamido-$\Delta^3$-desacetoxycephalosporanic acid S-sulfoxide. Fractions 70 upwards were evaporated to dryness and triturated with diethyl ether to obtain 1.6 g of crude product which was dissolved in 80 ml of ice-water to which sodium bicarbonate was added to adjust the pH to 8. The solution was washed with ethyl acetate and adjusted to pH 1.7 with 4N hydrochloric acid in the presence of 500 ml of ethyl acetate. The ethyl acetate layer was then washed with water, dried and concentrated to about 25 ml and the crystallizine solid was filtered off, washed with ethyl acetate and diethyl ether and dried to give 1.1 g (3 mmoles) of 7-phenylacetamido-$\Delta^3$-desacetoxycephalosporanic acid R-sulfoxide having a melting point of 180° C (with decomposition) and a specific rotation $[\alpha]_D = -71°$ (c=1% in 1 molar phosphate buffered at 8). PMR Spectrum (as the sodium salt in $D_2O$; the sodium salt of 2,2-dimethyl-2-silapentyl sulfonate was used as the internal standard): $\Delta$ (values in ppm): 1.93 (3H, s); 3.42, 4.00 (2H, AB-q; J = 17 Hz); 3.66 (2H, s); 4.77 (1H, d; J = 4.5 Hz); 5.46 (1H. d; J = 4.5 Hz); 7.33 (5H, s).

UV Spectrum $\lambda_{max} = 256$ nm. $E_{1\%}^{1cm} = 256$ (in $H_2O$, as the potassium salt)

IR Spectrum/(KBr)$\nu_{max}$ = 3340; 1780, 1709 1698; 1525; 1000.

Analysis: Calculated C: 55.17%, H: 4.60%, N: 8.05%, S: 9.19%. Found: C: 55.24%, H: 4.63%, N: 8.05%, S: 9.10%.

An ethereal solution of diazomethane was added to a solution of 100 mg (0.3 mmole) of 7-phenylacetamido-Δ³-desacetoxycephalosporanic acid R-sulfoxide in 5 ml of tetrahydrofuran until a light yellow color was noted. It was stirred for about 1 hour. After addition of 25 ml of diethyl ether, the reaction mixture was cooled to about 0° C and the methyl ester of 7-phenylacetamido-Δ³-desacetoxycephalosporanic acid R-sulfoxide crystallized to obtain a yield of 87 mg (0.25 mmole).

PMR Spectrum (in CDCl₃: tetramethylsilane was used as the internal standard), Δ (values in ppm); 2.19 (3H, s); 3.34, 4.02 (2H, AB-q); 3.57 (2H, s); 3.80 (3H, s); 4.46 (1H, d, J = 4.5 Hz); 5.25 (1H, q; J = 8 Hz and J = 4.5 Hz); 7.18 (1H, d, J = 8 Hz); 7.26 (5H, s).

IR Spectrum (KBr): $\nu_{max}$: 3300; 1780, 1730 1658; and 1060.

Mass Spectrum 362 (M₊), 314, 286, 270, 227, 195, 152, 140, 109, 91.

EXAMPLE 2

Preparation of
7-phenylacetamido-Δ³-desacetoxycephalosporanic acid R-sulfoxide 6.6 ml (55 mmoles) of a 30% aqueous hydrogen peroxide solution were added at about 5° C to a solution of 6.6 g (20 mmoles) of 7-phenylacetamido-Δ³-desacetoxycephalosporanic acid in 100 ml of methanol and then in the dark with vigorous stirring, 300 ml (60 mmoles) of an aqueous sodium hypochlorite solution (about 3.2 mmoles) were added below the surface from a burette with a capillary tip over a period of 90 minutes at about 5° C. A thin-layer chromatography check then showed that virtually all starting material had disappeared and that a mixture of equal amounts of 7-phenylacetamido-Δ³-desacetoxycephalosporanic acid R- and S-sulfoxides had been formed. The reaction mixture was concentrated in vacuo and extracted several times with ethyl acetate at pH 1.5. After drying over sodium sulfate, the ethyl acetate solution was concentrated until the onset of crystallization. Filtration yielded 3.2 g (9.2 mmoles) of 7-phenylacetamido-Δ³-desacetoxycephalosporanic acid S-sulfoxide and the filtrate was evaporated in vacuo to give a crude product which was worked up as described in Example 1 to obtain 1.2 g (3.5 mmoles) of 7-phenylacetamido-Δ³-desacetoxycephalosporanic acid R- sulfoxide. The product was characterized by PMR and IR spectra.

EXAMPLE 3

Preparation of
7-phenylacetamido-Δ³-desacetoxycephalosporanic acid R-sulfoxide 2.1 g (6.6 mmoles) of triphenyl phosphite were dissolved in a mixture of 25 ml of methanol and 50 ml of methylene chloride with stirring and the resulting solution was cooled in a dry ice-acetone bath at −78° C and then ozonized with a Fischer Model OZ II ozonator. Ozone was supplied at a rate of approximately 100 mmoles/hour and when the blue color of excess ozone was observed, the ozone stream was disconnected and replaced by a stream of dry nitrogen. Nitrogen purging was carried on well beyond the time necessary for the solution to loose its blue color. Then, a cold solution (−78° C) of 2.2 g, (6.6 mmoles) of 7-phenylacetamido-Δ³-desacetoxycephalosporanic acid in 20 ml of methylene chloride and 20 ml of methanol was added thereto after which the cooling bath at a temperature of −78° C was removed and the clear solution warmed to −27° C. The reaction mixture was kept at this temperature for 1 hour and was then permitted to warm up to room temperature. After stirring for another 2.5 hours during which gas evolution occurred, the mixture was diluted with 50 ml of water and adjusted to a pH of 8 with sodium bicarbonate. The organic layer was extracted several times with water at a pH of 8. Accordingly to a thin-layer chromatogram, about equal parts of the desired R- and S-sulfoxides had been formed. After treatment of the combined aqueous layers with decolorizing charcoal and adjustment of the pH to 1.7 in the presence of ethyl acetate, the aqueous layer was extracted several times with ethyl acetate. The combined ethyl acetate layers (250 ml) were concentrated in vacuo to about 30 ml until the onset of crystallization. Filtration yielded 600 mg (1.7 mmole) of 7-phenylacetamido-Δ³-desacetoxycephalosporanic acid S-sulfoxide and the filtrate was evaporated in vacuo to give a yellow solid which was chromatographed on a column (30cm in length, 4.3 cm in diameter) filled with 285 g of silica gel. The eluent was a 95:5 (v/v) mixture of acetone and acetic acid. Fractions 100 upwards were evaporated to dryness and the crude residue was worked up as described in Example 1 to yield 83 mg of 7-phenylacetamido-Δ³-desacetoxycephalosporanic acid R-sulfoxide (0.24 mmole). The product was confirmed by its IR spectrum and thin-layer chromatography.

EXAMPLE 4

Preparation of
7-(2-thienyl-acetamido-Δ³-cephalosporanic acid R-sulfoxide 10 mg of methylene blue were added to a solution of 2.7 g of 7-(2-thienyl-acetamido)-cephalosporanic acid (otherwise known as "cephalotin" ) in 1 liter of methanol and while air was passed therethrough, the solution was irradiated with a 1000 W lamp for 23 hours at 20° C. After 8 and 16 hours of irradiation respectively, a second and a third portion of 10 mg of methylene blue were added and then the solution was evaporated to dryness. The residue was dissolved in 100 ml of methanol and 15 g of silica gel were added and the solvent was removed in vacuo. The paste obtained was placed on the top of a column (1.8 cm in diameter, 30 cm in length) filled with silica gel. The successively used eluents were ethyl acetate and ethyl acetate containing 5% by volume of acetic acid. The first three 25 ml fractions contained cephalotin in the pure state and fractions 4 to 16 contained a mixture of compounds, but mainly relatively small amounts of cephalotin and cephalotin R-sulfoxide. As fraction 17 contained only the desired R-sulfoxide, the eluent was changed to ethyl acetate and acetic acid and fraction 17 upwards were collected and concentrated to small volume in vacuo, n-heptane was added and the removal of solvent continued until crystallization took place. After standing overnight at 3° C, the crystals of 7-(2-thienyl-acetamido)-cephalosporanic acid R-sulfoxide were collected by filtration and washed with diethyl ether to obtain a Yield of 840 mg (29%).

Analysis of the PMR spectrum of a solution of the final product in hexadeuterodimethylsulfoxide (60 Mc, Δ-values in ppm, 2,2-dimethyl-silapentane-5-sulfonate as internal reference):

| | |
|---|---|
| 2.07 (s, 3H) | |
| 3.45, 3.73. 4.10 and 4.38 (AB-quartet, $J \approx 16.5$ cps) | (4H) |
| 3.83 (s) | |
| 4.57, 4.78, 4.99 and 5.20 (AB-quartet, $J \approx 12.5$ cps) | (3H) |
| 4.81 and 4.89 (d, $J_{AB} \approx 4.6$ cps | |
| 5.56, 5.64, 5.69 and 5.77 (q, $J_{AB} \approx 4.6$ cps, $J' \approx 8.0$ cps, 1H) | |
| ~6.98 (2H); ~7.4 (1H); 9.25 (d, $J \approx 8.0$ cps, about 0.9H). | |

Partial analysis of the IR spectrum of the final product (KBr disc, values in cm$^{-1}$): ± 3350, ± 2550, 1790, 1737, ± 1718, 1680, 1230, 1040.

EXAMPLE 5

Preparation of 7-[3-(2,6-dichlorophenyl)-isoxazol-5-yl-acetamido]-Δ$^3$-cephalosporanic acid R-sulfoxide The irradiation of 2.75 g of 7-[3-(2,6-dichlorophenyl)-isoxazol-5-yl-acetamido]-cephalosporanic acid in 1 liter of methanol in the presence of a total amount of 30 mg of methylene blue was carried out exactly as described in Example 4. The product in the form of a paste on silica gel was placed at the top of a column (2.8 cm in diameter, 60 cm in length) filled with silica gel. Unreacted material was eluted with a 1:3 mixture of diethyl ether and ethyl acetate (about 1 l.). Mixed fractions were obtained by elution with about 1 l. of ethyl acetate and 1 l. of ethyl acetate containing 1% (v/v) of acetic acid respectively. Pure 7-[3-(2,6-dichlorophenyl)-isoxazol-5-yl-acetamido]cephalosporanic acid R-sulfoxide was finally eluted with acetone containing 5% (v/v) of acetic acid for a Yield of 840 mg (28%).

Analysis of the PMR spectrum of a solution of the R-sulfoxide in hexadeuterodimethylsulfoxide (60 Mc,Δ-values in ppm, 2,2-dimethyl-silapentane-5-sulfonate as internal reference):

| | |
|---|---|
| 2.07 (s, 3H) | |
| 3.40→4.35 (AB-q, $J_{AB} \approx 17$ cps) | (4H) |
| 4.05 (s) | |
| 4.59, 4.81, 4.99 and 5.21 (AB-q, $J \approx 12.7$ cps) | (3H) |
| 4.84 and 4.92 (d, $J_{AB} \approx 4.7$ cps) | |
| 5.7 (q, $J_{AB} \approx 4.7$ cps, J' $\approx$ 8.0 cps, 1H) | |
| 6.60 (s, 1H) | |
| 7.62 (narrow splitting pattern, 3H) | |
| 9.55 (d, J' $\approx$ 8.0 cps, about 0.8H) | |

Partial analysis of the IR spectrum of the final product (KBr disc, values in cm$^{-1}$): ±3400, ± 2550, 1785, 1735, 1715, 1680, 1600, 1430, 1390, 1230, 1040, 788.

EXAMPLE 6

Preparation of 7-(3-methylisoxazol-5-yl-acetamido)Δ$^3$-cephalosporanic acid R-sulfoxide 30 mg of methylene blue were added to a solution of 5.9 g of 7-(3-methylisoxazol-5-yl-acetamido)-cephalosporanic acid in 1.3 liter of methanol and while pure oxygen was passed through, the solution was irradiated with a 1000 W lamp for 21 hours at −30° C. According to thin-layer chromatograms, at least 40% of the starting material was converted predominantly to the R-sulfoxide and much smaller amounts of the S-sulfoxide and of a few degradation products. As usual, the solution was concentrated in vacuo to about 100 ml and the concentrated solution was kept at 3° C for about 60 hours. The crystalline precipitate so formed was filtered off, washed with diethyl ether and dried in vacuo. This product weighed 0.75 g and according to a thin-layer chromatogram and a PMR spectrum, this product was the R-sulfoxide contaminated with about 5% of the S-sulfoxide.

The filtrate was subsequently evaporated and the residue was subjected to column chromatography in the usual manner to obtain 3.0 g of starting material in pure crystalline state. Elution of the remaining R-sulfoxide was, somewhat unexpectedly, rather difficult. Only a part could be recovered. This second crop weighed 0.22 g and was completely pure.

Analysis of the PMR spectrum of a solution of 7-(3-methylisoxazol-5-yl-acetamido)cephalosporanic acid R-sulfoxide in hexadeuterodimethylsulfoxide (60 Mc,Δ-values in ppm, 2,2-dimethyl-silapentane-5-sulfonate as internal reference):

| | |
|---|---|
| 2.07 (s, 3H); 2.23 (s, 3H); 3.5→4.4 (AB-q, $J_{AB} \approx 17$ cps) | (4H) |
| 3.83 (s) | |
| 4.56, 4.78, 4.99 and 5.21 (AB-q, $J_{AB} \approx 13$ cps) | (3H) |
| 4.84 and 4.92 (d, $J_{AB} \approx$ 4.7 cps) | |
| 5.7 (q, $J_{AB} \approx 4.7$ cps, J' ~8.0 cps, 1H) | |
| 6.23 (s, 1H) | |
| 9.4 (d, J' $\approx 8.0$ cps, about 0.8H) | |

Partial analysis of the IR spectrum of 7-(3-methylisoxazol-5-yl-acetamido)cephalosporanic acid R-sulfoxide (KBr-disc, values in cm$^{-1}$): 3350; ± 2550; 1800; 1740; 1705; 1680; 1640; 1610; 1525; 1420; 1380; 1235; ± 1040.

EXAMPLE 7

Preparation of 7-(3-methylisoxazol-5-yl-acetamid)Δ$^3$-desacetoxycephalosporanic acid R-sulfoxide The oxidation reaction using 3 g of 7-(3-methyl-isoxazol-5-yl-acetamido)-desacetoxycephalosporanic acid as starting material was carried out exactly as described in Example 4 and 770 mg of pure starting material and 120 mg of pure but slightly wet the R-sulfoxide were obtained.

Analysis of the PMR spectrum of a solution of 7-(3-methylisoxazol-5-yl-acetamido desacetoxycephalosporanic acid R-sulfoxide in a mixture of hexadeuterodimethylsulfoxide and a small amount of dideuteroformic acid (60 Mc, Δ-values in ppm, 2,2-dimethyl-silapentane-5-sulfonate as internal reference):

| | |
|---|---|
| 2.10 (s, 3H) | |
| 2.22 (s, 3H) | |
| 3.4→4.3 (AB-q, $J_{AB} \approx$ 17 cps) | (4H) |
| 3.83 (s) | |
| 4.74 and 4.81 | AB-q, $J_{AB} \approx$ 4.5 cps, 2H |
| 5.61 and 5.68 | |
| 6.24 (s, 1H) | |
| 9.4 (d, J' $\approx$ 7.5 cps), visible in the spectrum of the solution without added formic acid) | |

Partial analysis of the IR spectrum of the final product (KBr-disc, values in $cm^{-1}$): ± 3400; ± 2550; 1780; ± 1715; 1680; 1615; 1420; 1380; 1540; 1040.

EXAMPLE 8

Preparation of
7-[3-(2,6-dichlorophenyl)-isoxazol-5-yl-acetamido]Δ³-desacetoxycephalosporanic acid R-sulfoxide.

The oxidation reaction using a solution of 4.9 g of 7-[3-(2,6-dichlorophenyl)-isoxazol-5-yl-acetamido]-desacetoxycephalosporanic acid in 1.3 liters of methanol was carried out as described in Example 4, including the use of a total of 30 mg of methylene blue added in two 15 mg portions. The reaction was stopped after 15 hours and after removal of solvent, the residue was submitted to column chromatography over silica. Practically quantitative elution was realized with a 99:1 mixture of acetone and acetic acid but separation of starting material and R-sulfoxide was poor. Only 220 mg of practically pure 7-[3-(2,6-dichlorophenyl)-isoxazol-5-yl-acetamido]-desacetoxycephalosporanic acid R-sulfoxide could be separated from the mixture in the first run.

Analysis of the PMR spectrum of a solution of the final product in hexadeuterodimethylsulfoxide (60 Mc, Δ-values in ppm, 2,2-dimethyl-silapentane-5-sulfonate as internal reference):

2.08 (s, 3H); 3.45→4.3 (AB-q, $J_{AB} \approx$ 16.5 cps)
4.00 (s) } (4H)
4.76 and 4.83 (d, $J_{AB} \approx$ 4.5 cps, 1H); ~5.65 (q, $J_{AB} \approx$ 4.5 cps, J'≈8.0 cps, 1H); 6.60 (s, 1H); 7.62 (narrow splitting pattern, 3H) 9.5 (d, J'≈8.0 cps, about 0.9H).

Partial analysis of the IR spectrum of the final product (KBr-disc, values in $cm^{-1}$): ± 3400, ± 2550; 1780; ± 1700; 1680; 1600; ± 1540; 1430; 1390; 1040; 792.

EXAMPLE 9

Preparation of
7-[D-(N-2.2.2-trichloroethyloxycarbonyl)-α-amino-benzylcarbonamido]Δ³-desacetoxycephalosporanic acid R- sulfoxide.

The irradiation of a solution of 3.0 g of 7-[D-(N-2.2.2-trichloroethyloxycarbonyl)-α-amino-benzylcarbonamido]-desacetoxycephalosporanic acid (N-trichloroethyloxycarbonyl-cephalexin) in 1.3 liters of methanol to which was added a total of 30 mg of methylene blue was carried out as described in Example 4. The reaction was discontinued after 29 hours when thin-layer chromatograms indicated well over 50% conversion of the starting product. After evaporation of solvent, the residue was absorbed on 15 g of silica gel in the usual fashion and separation of the R-sulfoxide was carried out with column chromatography employing 350 g of silica gel and a 97:3 mixture of acetone and acetic acid. The fractions solely containing R-sulfoxide were combined and concentrated in vacuo to small volume, upon which n-heptane was added to remove acetic acid by further concentration in vacuo. Since precipitation of solid material did not take place, solvent was removed completely and the residue was dissolved in methanol. The solution in methanol was treated with activated carbon, filtered and concentrated to small volume. Dry ethyl acetate was added and concentration in vacuo continued. Addition of n-heptane to the concentrated solution of the product in ethyl acetate resulted in a solid precipitate. The product was vacuum filtered, repeatedly washed with n-heptane and dried in vacuo to obtain 1.04 g of final product whose structure was confirmed by IR and PMR spectra: IR (KBr): ± 3500 and ± 2600; ±3400 and ± 3300; 1780; 1725; 1685; ± 1500–1540; 1240; 1050 (values in $cm^{-1}$). PMR (d₆-DMSO+1 droplet of DCOOD, 60 Mc, Δ-values in ppm): 2.1 (s, 3H); 3.3–4.1 (q, 2H); 4.7 (d, 1H); 4.85 (s, 2H); 5.45 (d) and ±5.6 (q) together 2H; 7.4 (5H); 8.5 (d, about 1 H); 9.4 (d, about 1H).

EXAMPLE 10

Preparation of
7-[D-α-amino-benzylcarbonamido]Δ³-desacetoxycephalosporanic acid R-sulfoxide(cephalexin-R-sulfoxide)

500 mg of N-trichloroethyloxycarbonyl-cephalexin-R-sulfoxide (prepared according to Example 9) were dissolved at 0° C in 31 ml of 90% of formic acid and after 300 mg of zinc powder were added, the mixture was stirred for 90 minutes at 0° C [this reduction method has been applied on N-trichloroethyloxycarbonyl-cephalexin itself, according to R. R. Chauvette et al., J. Org. Chem., Vol. 36, p. 1267 (1971).]Subsequently, the reaction mixture was filtered and somewhat concentrated in vacuo to be able to determine by thin-layer chromatography whether the starting product was completely reduced. Since this was not the case, the volume of the solution was increased to 30 ml with 90% formic acid and another 300 mg of zinc powder were added and the reaction mixture was stirred for approximately 90 minutes at 0° C. The reaction mixture was filtered, concentrated in vacuo to a small volume, and dry benzene added etc., till formic acid was removed completely. The residual yellowish syrup was mixed with 20 ml of water whereupon hydrogen sulfide was passed through at 0° C for 15 minutes. The suspension was cleared centrifugally and the resulting clear liquid was separated from the residue. The residue was stirred with water and the centrifugally obtained, clear washing was combined with the first filtrate and completely evaporated after addition of n-butanol. The residual solid weighed 380 mg after extensive drying in vacuo and this material was suspended in 10 ml of acetonitrile. When mixed with water, the pH of the suspension was 2.1. Subsequent addition of triethylamine to the suspension at 0° C till the mixture had attained a pH of 9.0 resulted in an almost clear solution. Residue and solution were separated centrifugally and the residue was extracted in the same way with 2 ml of acetonitrile. The yellow colored filtrates were combined and treated with 1N HCl till a pH of 6.0 was reached which resulted in a colorless solid precipitate. The precipitate collected by filtration was washed twice with 5 ml of acetonitrile and once with 10 ml of diethyl ether. After extensive drying at 1 mm Hg, the final product weighed 160 mg and the structure of the final product was confirmed by its IR and PMR spectra. The product was substantially pure except for the presence of about 0.7 mole of triethylamine HCl per mole of cephalexin-R-sulfoxide. IR (KBr): ± 3420; ± 3200; 1780; 1690; ± 1595; ± 1550; 1030 (values in $cm^{-1}$). PMR (mixture of d₆-DMSO and small amount of CF₃-COOD, 60 Mc, Δvalues in ppm): 2.05 (s, 3H); 3.4–4.25 (AB-q, J≈17 cps, 2H); 4.8 (d, J≈4.5 cps, 1H); 5.2 (broad s, 1H); ±5.8 (q-like, J≈4.5 cps; J'≈8 cps, 1H); ± 7.5 (5H); ± 8.8 (broad, partly exchanged, about 1.1H); 9.9 (d, J'≈8 cps, partly exchanged, about 0.5H). N(C₂H₅)₃ at 1.2 (t) and 3.1 (q).

EXAMPLE 11

A solution of 0.33 g (1 mmole) of 7-phenyl-acetamido-$\Delta^3$-desacetoxycephalosporanic acid, 0.3 ml (2mmoles) of triethylamine, 0.55 g (2 mmoles) of iodobenzenedichloride in 16 ml of acetonitrile and 2 ml of water was stirred for half an hour and then was poured into a mixture of 50 ml of water and 100 ml of ethyl acetate. After adjusting the pH to 1.7, the layers were separated, and the water layer was extracted several times with ethyl acetate. The combined ethyl acetate layers were concentrated to about 10 ml after which crystallization occurred.

After filtration of the crystalline S-sulfoxide, the mother liquor was treated with ligroin to obtain 0.11 g of crude 7-phenyl-acetamido-$\Delta^3$-desacetoxycephalosporanic acid R-sulfoxide. The structure was confirmed by TLC and IR.

EXAMPLE 12

0.3 g (1 mmole) of chloro amine T at 0° C were added to a solution of 0.3 g (1 mmole) of 7-phenylacetamido-$\Delta^3$-desacetoxycephalosporanic acid and 0.1 g of sodium bicarbonate in 5 ml of water. According to a thin-layer chromatogram check, about equal amounts of 7-phenylacetamido-$\Delta^3$-desacetoxycephalosporanic acid-R and S-sulfoxides appeared to be formed.

EXAMPLE 13

Preparation of 7-salicylideneamino-$\Delta^3$-desacetoxycephalosporanic acid R-sulfoxide 13.23 g of 7-salicylideneamido-desacetoxycephalosporanic acid were suspended in 125 ml of freshly distilled tetrahydrofuran and while cooling in an ice-bath, 8.44 g. of 3-chloroperbenzoic acid in 25 ml of THF were added at a rate such that the temperature did not rise above 10° C. Then, the mixture was stirred for another hour and after dry n-hexane was added, the formed precipitate was collected on a filter, washed with a mixture of n-hexane-diethyl-ether (1:1) and with diethyl ether. The yield of the desired sulfoxide was nearly quantitative and the structure was confirmed by IR- and PMR spectra.

IR (KBr): 3430, 1780, 1710, 1630, 1070, 1055, 1025.
PMR (DMSO-$d_6$): 2.05 (s, 3H); 3.60–4.32 (q. J=17.0 cps, 2H); 5.11 (d, J=4.0 cps, 1H); 5.75 (d/d, J=4.0 cps, J'=1.5 cps, 1H); 6.8–7.8 (arom. H, 4H); 8.87 (d, J'=1.5 cps, 1H); 11.57–12.23 (b, 1H).

EXAMPLE 14

Preparation of 7-amino-$\Delta^3$-desacetoxycephalosporanic acid R-sulfoxide (7-ADCA-R-sulfoxide)

300 mg of 7-salicylideneamino-desacetoxycephalosporanic acid R-sulfoxide were dissolved with cooling in an ice-bath in a 4N HCl solution. After stirring for 50 minutes, the reaction mixture was twice extracted with diethyl ether. The pH was adjusted to 2.7 and the desired product was precipitated. Collection of the product on a filter followed by washings with water and acetone afforded after drying 70% of the desired sulfoxide having the follwing characteristics:

IR (KBr): 1800, 1620, 1530, 1070, 1060, 800.
PMR (CF$_3$COOH + D$_2$O): 2.32 (s, 3H); 3.67–4.58 (q, J = 17.5 cps, 2H); 5.12 (d, J = 4.3 cps, 1H); 5.56 (d, J = 4.3 cps. 1H).

EXAMPLE 15

Preparation of 7-salicylideneamino-$\Delta^3$-cephalosporanic acid R-sulfoxide.

This compound was prepared using the procedure of example 13 with a 94% yield. The structure of the said sulfoxide was confirmed by IR (KBr): 3420, 1790, 1745, 1720, 1625, 1235, 1220, 1065, 1045, 1020.

PMR (DMSO-$d_6$) + some DCO$_2$D): 2.08 (s, 3H); 3.61–4.43 (q, J = 16.5 cps, 2H); 4.58–5.25 (q, J = 13.2 cps) and 5.21 (d, J = 4.3 cps, 3H); 5.80 (d/d, J = 4.3 cps, J' = 1.5 cps, 1H); 6.8–7.8 (arom. H, 4H); 8.83 (d, J' = 1.5 cps, 1H).

EXAMPLE 16

Preparation of 7-amino-$\Delta^3$-cephalosporanic acid R-sulfoxide (7-ACA R-sulfoxide)

Using the procedure of Example 14, the salicylidene compound was hydrolyzed in a minimum quantity of 4N HCl and after extraction, the pH was adjusted to 1.5. The sulfoxide product precipitated and was isolated in a 67% yield.

IR (KBr): 1800, 1740, 1620, 1550, 1510, 1240, 1070.
PMR (CF$_3$COOD): 2.30 (s, 3H); 3.97–4.87 (q, J = 17 cps, 2H); 5.00–5.52 (q, J = 14 cps) and 5.42 (d, J = 4.5 cps, 3H); 5.75 (d, J = 4.5 cps, 1H).

EXAMPLE 17

Preparation of 7-[3-(2.6-dichlorophenyl)-isoxazol-5-yl acetamido]-$\Delta^3$-desacetoxycephalosporanic acid R-sulfoxide.

1.24 g of 7-ADCA R-sulfoxide were silylated with trimethylchlorosilane and triethyl amine in ethyl acetate and after addition of quinoline thereto, a solution of 3-(2.6-dichlorophenyl)-isoxazol-5-yl-acetyl chloride [prepared from 1.5 g of 3-(2.6-dichlorophenyl)-isoxazol-5-yl acetic acid] in ethyl acetate was added. The temperature rose about 10° C and the reaction mixture was stirred for another hour at room temperature. Then, the mixture was hydrolyzed in water and extracted with ethyl acetate at a pH of 2.5. Concentration of the organic layer and addition of diethyl ether caused precipitation of the sulfoxide product that was isolated in a 48% yield. TLC, IR and PMR were identical with those of the compound prepared in Example 8.

EXAMPLE 18

Preparation of 7-[2-thienylacetamido]-$\Delta^3$-desacetoxycephalosporanic acid R-sulfoxide Starting from 1.24 g of 7-ADCA R-sulfoxide which was silylated with bistrimethylsilylacetamide and reacted with 2thienylacetyl chloride, 900 mg of the desired sulfoxide compound were isolated after extraction at a pH of 2.5 with ethyl acetate and n-butanol. The structure of the obtained compound was characterized by:

IR (KBr): 3330, 1790, 1700, 1635, 1010.
PMR (DMSO-$d_6$): 2.08 (s, 3H); 3.45–4.40 (q, J = 16.5 cps) and 3.82 (s), 4H; 4.69 (d, J = 4.5 cps, 1H); 5.58 (q, J = 4.5 cps, J' = 8.0 cps, 1H); 6.98 (2H); 7.4 (1H); 9.30 (d, J' = 8.0 cps).

EXAMPLE 19

Preparation of
7-[3-(2.6-dichlorophenyl)-5-methyl-isoxazol-4-yl
carbonamido]-Δ³-desacetoxycephalosporanic acid
R-sulfoxide Using the procedure of Example 17, 1.6 g of 3-(2.6-dichlorophenyl)-5-methyl-isoxazol-4-yl carbonyl chloride and 1.24 g of silylated 7-ADCA R-sulfoxide were reacted to obtain 600 mg of the desired sulfoxide product after extraction of the water layer with ethyl acetate at a pH of 3 and concentration of the combined organic layers. The isolated product was characterized by:

Ir (KBr): 3430, 1780, 1720, 1660, 1040, 795, 785.

PMR (DMSO-$d_6$): 2.07 (s, 3H); 2.77 (s, 3H); 3.75–4.22 (q, J = 16.5 cps, 2H); 4.76 (d, J = 4.5 cps, 1H); 5.74 (q, J = 4.5 cps, J' = 8.0 cps, 1H); 7.58 (arom. H, 3H); 9.27 (d, J' = 8.0 cps).

EXAMPLE 20

Preparation of
7-[2-thienylacetamido]-Δ³-cephalosporanic acid
R-sulfoxide

Using the procedure of Example 17. 1.55 g of 7-ACA R-sulfoxide were silylated in ethyl acetate with trimethylchlorosilane and after reaction with 2-thienylacetyl chloride at room temperature for 1 hour, 1150 mg (52% yield) of the desired sulfoxide compound were isolated after carrying out the same procedures. The obtained sulfoxide appeared to be the same as the product described in Example 4 according to its TLC, IR and PMR.

EXAMPLE 21

Preparation of
7-[phenylacetamido]-Δ³-cephalosporanic acid
R-sulfoxide.

Using the procedure of Example 17, 0.73 ml of phenylacetyl chloride with 1.55 g of 7-ACA R-sulfoxide silylated with trimethylchlorosilane in ethylacetate were reacted to give a yield of 67% of the desired sulfoxide compound after treating the reaction mixture in the same way as described above. The structure of the obtained compound was characterized by:

IR (KBr): 3350, 1785, 1730, 1720, 1660, 1230, 1030.

PMR (DMSO-$d_6$): 2.06 (s, 3H); 3.45–4.38 (q, J = 16.5 cps) and 3.58 (s), 4H; 4.57–5.20 (q, J = 13 cps) and 4.83 (d, J = 3.7 cps) 3H; 5.65 (q, J = 4.7 cps, J' = 8 cps); 7.30 (s, 5H); 9.20 (d, J' = 8 cps).

EXAMPLE 22

Preparation of
7-[phenylacetamido]-Δ³-cephalosporanic acid
R-sulfoxide by oxidation with N,N'-dichlorourethane 330 mg (1 mmole) of 7-phenylacetamido-Δ³-cephalosporanic acid in 10 ml of tetrahydrofuran were added with stirring to a cold solution (-60° C) of 160 mg (1 mmole) of N,N'-dichlorourethane in 5 ml of tetrahydrofuran and the mixture was stirred at -60° C for some time and TLC was made. After 10 minutes, all starting material had disappeared and the reaction mixture was poured into a mixture of 75 ml of ethyl acetate and 50 ml of water and the pH was adjusted to 1 with hydrochloric acid. After extracting the water layer several times with ethyl acetate, water was added to the combined organic layers and the pH was adjusted to 7 with a potassium hydroxide solution. Separating of the layers was followed by washing of the water layer with ethyl acetate. Then ethyl acetate was added to the water layer, after which the pH was adjusted to 1. After separation of the layers, the water layer was extracted several times with ethyl acetate. The combined ethyl acetate layers were dried over anhydrous magnesium sulfate and concentrated to obtain 74 mg (0.2 mmole) of crystalline material which was filtered off. According to TLC and spectral properties it appeared to be 7-phenylacetamido-Δ³-cephalosporanic acid R-sulfoxide.

EXAMPLE 23

Preparation of the hydrochloride of pivaloyloxymethyl
7-amino-Δ³-desacetoxycephalosporanate R-sulfoxide 3 ml (20 mmoles) of chloromethylpivalate were added to a suspension of 2.3 g (10 mmoles) of 7-amino-Δ³-desacetoxycephalosporanic acid R-sulfoxide and 2ml (14 mmoles) of triethylamine in 15 ml of dimethylformamide and after stirring for 22 hours, 30 ml of ethyl acetate were added. The precipitated triethyl ammonium chloride was filtered off and the filtrate was washed with ice water, dried over anhydrous magnesium sulfate and concentrated in vacuo to about 25 ml. 7.5 ml. 7.5 ml of a 1N hydrochloric acid solution in isopropanol were added to the concentrated solution. After precipitation with n-hexane, the precipitate was filtered off, washed with n-hexane and dried to obtain 1.7 g (4.4 mmoles) of the hydrochloride of the pivaloyloxymethylester of 7-amino-Δ³-desacetoxycephalosporanic acid R-sulfoxide.

PMR spectrum (in DMSO-$d_6$ and a trace of CDCl$_3$) 2.2-dimethylsilapentane-5-sulfonate as internal reference, 60 Mc,Δ-values in ppm: 1.45 (9H, s); 2.29 (3H,s); 3.85, 4.46 (2H, AB-q; J = 16 Hz); 4.67 (1H, d; J = 4.5 Hz); 5.32 (1H, d; J = 4.5 Hz).

IR spectrum (KBr): $\nu_{max}$: 3450, 3000, 1795, 1740, 1160, ca. 1050.

EXAMPLE 24

Preparation of the hydrochloride of pivaloyloxymethyl
7-[D-α-amino-benzylcarbonamido]-Δ³-desacetoxycephalosporanate R-sulfoxide A mixture of 1 g (5 mmoles) of the hydrochloride of phenylglycyl choride, 0.8 g (10 moles) of sodium bicarbonate, 1.5 g (4 mmoles) of the hydrochloride of pivaloyloxymethyl 7-amino-Δ³-desacetoxycephalosporanate R-sulfoxide and 20 ml of carefully dried methylene chloride was stirred vigorously at 0° C for 5 hours. After filtration and treatment with dicalite and decolorizing carbon, the filtrate was concentrated and then 20 ml of isopropanol and 50 ml of diethyl ether were added. After precipitation with n-hexane, the solid material obtained by filtration was washed with n-hexane and dried to obtain 1.3 g of the crude hydrochloride of pivaloyloxymethyl 7-[D-α-amino-benzylcarbonamido]-Δ³-desacetoxycephalosporanate R-sulfoxide.

IR spectrum (KBr):$\nu_{max}$:3400, 3000, 1795, 1730, 1695, 1160, ca. 1040, 700.

EXAMPLE 25

Preparation of pivaloyloxymethyl
7-phenylacetamido-Δ³-desacetoxycephalosporanate
R-sulfoxide After stirring a mixture of 0.39 g (1 mmole) of the potassium salt of 7-phenylacetamido-Δ³-desacetoxycephalosporanic acid R-sulfoxide, 0.6 ml (4 mmoles) of chloromethylpivalate and 4 ml of dimethylformamide for 43 hours at room temperature, the reaction mixture was layered with ethyl acetate. The organic layer was then washed with water, a sodium bicarbonate solution, again with water, dried over anhydrous sodium sulfate, and evaporated to dryness in vacuo. The residue was triturated with n-hexane and dried in vacuo to obtain 0.35 g (0.76 mmole) of pivaloyloxymethyl 7-phenyl acetamido-$\Delta^3$-desacetoxycephalosporanate R-sulfoxide.

PMR spectrum (in CDCl$_3$; tetramethylsilane was used as the internal reference; 60 Mc) ($\Delta$values in ppm); 1.47 (s,9); 2.27 (s,3); 3.38; 4.04 (AB-q, 2; J = 17Hz); 4.48 (d,1; J = 4.5 Hz); 4.63 (s,2); 5.26 (q,1; J$^1$ = 8 Hz, J = 4.5 Hz); 7.08 (d, 1; J$^1$ = 8Hz); 7.24 (s,5).

IR spectrum (KBr)$\nu_{max}$: 3280; 2980; 1780; 1760; 1730; 1700; 1040.

EXAMPLE 26

A. The preparation of 7-(D-2,2-dimethyl-5-oxo-4-phenyl-1-imidazolidinyl)-$\Delta^3$-desacetoxycephalosporanic acid A mixture of 0.95 g (2.7 mmoles) of cephalexin, 0.8 ml (6 mmoles) of triethylamine and 5 ml of acetone was stirred for 48 hours at 0° C and after centrifugation, the clear decanted liquid was added slowly to 5 ml of water while the pH was kept between 2.5 and 3 with sulfuric acid. After stirring for 3 hours at 0° C, the precipitate was filtered off and the filtrate was extracted with ethyl acetate. The ethyl acetate layers were concentrated in vacuo and stirred with diethyl ether and after filtration, the precipitate was dried to obtain 0.27 g (0.7 mmole) of 7-(D-2,2-dimethyl-5-oxo-4-phenyl-1-imidazolidinyl)-$\Delta^3$-desacetoxycephalosporanic acid. PMR spectrum (in hexadeutero dimethyl sulfoxide; tetramethylsilane was used as an internal reference).

($\Delta$-vales in ppm): 1.30 (s,3); 1.40 (s,3); 2.04 (s,3); 3.27 and 3.31 (s,1; s,1); 4.61 (s,1); 4.90→5.20 (d,1 and q, 4; J = 4.5 Hz; J ≈ 8Hz); ≈6.30 (broad signal; 1); 7.10→7.50 (narrow splitting pattern, 5).

B. The preparation of 7-(D-2,2-dimethyl-5-oxo-4-phenyl-1-imidazolidinyl)-$\Delta^3$-desacetoxycephalosporanic acid R-sulfoxide A mixture of 0.77 g (0.2 mmole) of 7-(D-2,2-dimethyl-5-oxo-4-phenyl-1-imidazolidinyl)-$\Delta^3$-desacetoxy-cephalosporanic acid, 0.62 g (0.54 mmole) of 3-chloro-perbenzoic acid and 4 ml of acetonitrile was stirred for 4.5 hours at 0° C and then was filtered. To the filtrate was added slowly n-heptane until no more precipitate was obtained and the precipitate was filtered off and dried to obtain 0.57 g (0.15 mmole) of the 7-(D-2,2-dimethyl-5-oxo-4-phenyl-1-imidazolidinyl)-66 $^3$-desacetoxycephalosporanic acid R-sulfoxide.

PMR spectrum (in hexadeutero dimethyl sulfoxide 60 Mc; 2,2-dimethyl-silapentane-5-sulfonate as an internal reference) ($\Delta$values in ppm): 1.42 (s,3); 1.49 (s,3); 2.01 (s,3); 3.46 and 4.13 (Ab-q,2; J = 16.5 Hz); 4.50 (s,1); 4.68 (d,1; J = 4.5 Hz); 5.55 (d,1; J = 4.5 Hz); 7.41 (s,5); 8.33 (s,1).

IR spectrum (KBr disc; partial analysis) $\nu_{max}$: 3400; 2950, 1790; 1710; 1020; 1040.

EXAMPLE 27

The preparation of benzylpenicillin R-sulfoxide 5 ml of water and 3 g (10 mmoles) of iodobenzene dichloride in 40 ml of pyridine were added at -10° C with stirring to a suspension of 7.1 g (20 mmoles) of the sodium salt of benzylpenicillin in 160 ml of pyridine. The solution was stirred for 90 minutes and was poured into 200 ml of water and 500 ml of ethyl acetate. After adjusting the pH to 1.7 with HCl and extraction of the water layer several times with ethyl acetate, the combined organic layers were dried, concentrated and treated with diethyl ether and n-hexane. The obtained precipitate (3 g) was dissolved in water and sodium bicarbonate and the resulting solution was washed with methylene chloride, treated with decolorizing carbon, adjusted to a pH of 1.7 with HCl in the presence of methyl isobutylketone and extracted with methyl isobutylketone. The dried, concentrated organic layer was treated with diethyl ether and n-hexane and the precipitate was filtered off and dried to obtain 1.9 g of a mixture of benzylpenicillin, benzylpenicillin R-sulfoxide and benzylpenicillin-S-sulfoxide. 1.4 g of this precipitate was chromatographed on a column (65 cm in length, 2.5 cm in diameter filled with 180 g of silica gel and the eluent was a 97:3 (v/v) mixture of acetone and acetic acid. Fractions 30 to 71 contained 115 mg of the benzylpenicillin R-sulfoxide which was isolated by evaporating the solvent and dissolving the residue in ethyl acetate followed by precipitation with diethyl ether and n-hexane.

PMR spectrum (in DMSO-d$_6$, tetramethylsilane was used as an internal reference, $\Delta$-values in ppm): 1.25 (s,3); 1.58 (s,3); 3.58 (s,2); 4.09 (s,1); 4.70 (d,1; J = 4 Hz); 5.45 (q.1; J = 7.5 Hz and J = 4 Hz); 7.28 (s,5); 9.24 (d,1; J = 7.5 Hz). IR spectrum (KBr): 1785, 1660, 1040 cm$^{-1}$.

EXAMPLE 28

The preparation of phenoxymethylpenicillin R-sulfoxide

The title compound was prepared as described by Spry in J.A.C. S. Vol. 92, 5006 (1970) as follows: A solution of 3.5 g (10 mmoles) of phenoxymethylpenicillin in 1 liter of an 1:1 (v/v) mixture of acetone and water was treated with ozone at a rate of 3.4 g/hr for 2.5 hours at 15° C. Evaporation of acetone after filtration and drying gave 1.4 g of the S-sulfoxide. After extracting the filtrate at pH 2.3 with 3 × 100 ml of ethyl acetate, the ethyl acetate was evaporated and trituration of the residue gave 1.1 g of the phenoxymethylpenicillin R-sulfoxide.

PMR spectrum: (in CDCl$_3$ and DMSO-d$_6$; tetramethylsilane was used as an internal reference; $\Delta$-values in ppm); 1.32 (s,3); 1.68 (s,3); 4.33 (s,1); 4.58 (s,2); 4.66 (d,1; J = 4.5 Hz); 5.43 (q, 1; J = 8 Hz and J = 4.5 Hz); 6.8-7.4 (m,5); 8.89 (d,1; J = 8 Hz).

EXAMPLE 29

The preparation of 6-[3-(2,6-dichlorophenyl)-5-methyl-isoxazol-4-yl-carboxamido]-penicillanic acid R-sulfoxide 0.55 g (2 mmoles) of iodobenzene dichloride were added in 10 minutes at −10° C to a mixture of 0.45 g (1 mmole) of dicloxacillin, 8 ml of pyridine and 1 ml of water. After stirring for 90 minutes at −10° C, the reaction mixture was poured into 50 ml of ice water and 100 ml of ethyl acetate. After adjusting the pH to 1.7, the layers were separated and the water layer was extracted with 3 × 50 ml of ethyl acetate. The combined organic layers were washed, dried, concentrated and treated with diethyl ether and n-hexane to obtain dicloxacillin R-sulfoxide which was filtered off and dried for a yield of 0.17 g of the product desired.

PMR spectrum (in DMSO-$d_6$; tetramethylsilane was used as an internal reference; Δ-values in ppm); 1.21 (s,3); 1.48 (s,3); 2.74 (s,3); 4.25 (s,1); 4.72 (d,1; J = 4 Hz); 5.50 (q,1; J = 7.5 Hz and J = 4 Hz); 7.58 (s,5); 9.23 (d,1: J = 7.5 Hz).

EXAMPLE 30

The preparation of phenylacetamido-$\Delta^3$-desacetoxycephalosporanic R-sulfoxide 14.5 g (170 mmoles) of sodium bicarbonate and 150 ml of methanol, 50 ml of an aqueous $H_2O_2$ solution (28%) and 4 ml (160 mmoles) of bromine in 50 ml of methanol were simultaneously supplied to a vigourously stirred mixture of 1 g (3 mmoles) of phenylacetamido-66 3-cephalosporanic acid, below the surface from burettes with a capillary tip over a period of 2½ hours at a rate so that no brown color appeared. The reaction was carried out at 35° C in the dark. After the colorless reaction mixture was cooled in ice and diluted with 300 ml water, the methanol was distilled off. Then the solution was extracted at a pH=1.7 with ethyl acetate, and after the ethyl acetate was evaporated, the crude residue was dissolved in water with sodium bicarbonate. This solution was treated with decolorizing carbon and extracted with ethyl acetate at a pH = 1.7. After concentrating the ethyl acetate and trituration with ligroin, 53 mg of a mixture of phenylacetamido-$\Delta^3$-desacetoxycephalosporanic-R and S-sulfoxide were obtained (according to TLC; bio-autogram and IR-spectrum), containing about 80% of the R-sulfoxide.

EXAMPLE 31

From the compounds obtained in Examples 1 to 8, 10, 11, 17 to 22 and 26 to 29 a dry powder for injection was prepared as follows: A quantity of 100 to 2000 mg of the sterile sodium salt of the desired compound was aseptically introduced under a nitrogen atmosphere into a vial suitable for injectable compositions. The vials were closed by rubber plates which were fixed in their position by aluminum joint rings to eliminate the exchange of gases or the penetration of microorganisms. Before use, the powder was dissolved in a suitable amount of sterile and pyrogen-free water.

EXAMPLE 32

From the compounds obtained in Examples 1 to 8, 10, 11, 17 to 22 and 26 to 29, syrups were prepared by mixing the following ingredients:
sodium salt of the sulfoxide compound — 1.5 - 6 g
soluble starch — 1 - 3 g
sodium saccharin — 0.1 - 1 g
methyl p-hydroxybenzoate — 0.06 g
strawberry flavor — 0.1 - 5 g
amaranth — 0.010 g
saccharose — 30 g
water added to a volume of — 60 ml
These syrups were useful for oral administration.

EXAMPLE 33

Capsules were prepared in the usual way containing as active ingredient the compounds obtained in Examples 1 to 3, 10, 11, 17 to 22 and 26 to 29. The components of the capsules are specified below:
sodium salt of the sulfoxide compound — 150–500 mg
potassium bicarbonate — 100–300 mg
magnesium stearate — 2–10 mg
lactose — quantity sufficient for 1 capsule.
These capsules can be used for oral administration.

EXAMPLE 34

Tablets were prepared in the usual way containing as active ingredient the compounds obtained in Examples 1 to 8, 10, 11, 17 to 22 and 26 to 29. The components of the tablets are listed below:
sodium salt of the sulfoxide compound — 125–500 mg
polyvinylpyrrolidone — 5–30 mg
amylum maidis — 100–300 mg
magnesium stearate — 1–20 mg
lactose — quantity sufficient for a tablet.
These tablets can be used for oral administration.

ANTIBACTERIAL STUDY

The antibacterial activity were determined with an agar serial dilution test as follows:

A stock solution of the antibiotic at 2,000 μg/ml is prepared in a sterile suitable vehicle. Two-fold dilutions are made with sterile 1/20 mol. phosphate buffer pH 6.5 ($KH_2PO_4$ - NaOH). 1 ml quantities of each dilution are incorporated in 19 ml of brain-heart infusion agar in sterile Petri dishes. The hardened surface is inoculated with test organisms and incubated 24 hours at 37° C. The minimal inhibitory concentration (MIC), i.e. the least amount of antibiotic that completely inhibits the test organism, is expressed in μg/ml. The results obtained are reported in Table 1. The following compounds were tested and reported:

A. 7-[3-methyl-isoxazol-5-yl-acetamido]-$\Delta^3$-cephalosporanic acid R-sulfoxide.
B. 7-[3-methyl-isoxazol-5-yl-acetamido]-$\Delta^3$-desacetoxycephalosporanic acid R-sulfoxide.
C. 7-Phenylacetamido-$\Delta^3$-desacetoxycephalosporanic acid S-sulfoxide.
D. 7-Phenylacetamido-$\Delta^3$-desacetoxycephalosporanic acid R-sulfoxide.
E. 7-Phenylacetamido-$\Delta^3$-desacetoxycephalosporanic acid.
F. 7-(2-thienyl-acetamido)-$\Delta^3$-cephalosporanic acid.
G. 7-(2-thienyl-acetamido)-$\Delta^3$-cephalosporanic acid R-sulfoxide.
H. 7-(2-thienyl-acetamido)-$\Delta^3$-cephalosporanic acid S-sulfoxide.
I. 7-[3-(2,6-dichlorophenyl)-isoxazol-5-yl-acetamido]-$\Delta^3$-cephalosporanic acid R-sulfoxide.
J. 7-α-amino phenylacetamido-$\Delta^3$-desacetoxycephalosporanic acid.
K. 7-α-amino phenylacetamido-$\Delta^3$-desacetoxycephalosporanic acid R-sulfoxide.
L. 7-α-amino phenylacetamido-$\Delta^3$-desacetoxycephalosporanic acid S-sulfoxide.
M. 7-[3-(2,6-dichlorophenyl)-isoxazol-5-yl-acetamido]-$\Delta^3$-desacetoxycephalosporanic acid R-sulfoxide.
N. 7-[3-(2,6-dichlorophenyl)-isoxazol-5-yl-acetamido]-$\Delta^3$-desacetoxycephalosporanic acid.
O. 6-[3-(2,6-dichlorophenyl)-5-methyl-isoxazol-4-yl-carboxamido]-penicillanic acid R-sulfoxide.
P. 6-[3-(2,6-dichlorophenyl)-5-methyl-isoxazol-4-yl-carboxamido]-penicillanic acid S-sulfoxide.
Q. 6-Phenylacetamido-penicillanic acid R-sulfoxide.
R. 6-Phenylacetamido-penicillanic acid S-sulfoxide.
S. 6-Phenoxyacetamido-penicillanic acid R-sulfoxide.
T. 6-Phenoxyacetamido-penicillanic acid S-sulfoxide.

| Strain of Bacteria | A | B | C | D | E | F | G | H | I | J | K | L | M | N |
|---|---|---|---|---|---|---|---|---|---|---|---|---|---|---|
| Gram positive | | | | | | | | | | | | | | |
| Bacillus subtilis ATCC 6633 | 0.25 | 0.5 | 25 | 0.12 | 0.5 | 0.12 | 0.7 | 6 | 0.12 | 0.5 | 1.5 | 50 | 0.06 | 1 |
| Staphylococcus aureus A 55 | — | — | >100 | 3 | 6 | 0.25 | 0.7 | 12.5 | 1 | 3 | — | — | — | 0.75 |
| ( A 321 | 3 | 6 | >100 | 3 | 1.5 | 0.5 | 1.5 | 12.5 | 1 | 1.5 | 12.5 | >100 | 0.06 | 0.5 |
| A 355') | 6 | 50 | >100 | 6 | 100 | 0.5 | 3 | 12.5 | 3 | 12.5 | 50 | >100 | 0.25 | 3 |
| L160a') | — | — | >100 | 6 | 12.5 | 0.5 | 6 | 12.5 | 3 | 12.5 | — | — | — | 1.5 |
| Streptococcus haemolyticus A 266 | 0.12 | 0.25 | 25 | 0.06 | 1 | <0.06 | 0.1 | 0.2 | 0.03 | 0.25 | 1.5 | 50 | 0.03 | 0.5 |
| Streptococcus faecalis L 80 | 50 | >100 | >100 | 50 | >100 | 25 | 12.5 | >50 | 3 | 100 | 100 | >100 | 3 | 12.5 |
| Diplococcus pneumoniae L 54 | 0.5 | 1.5 | 100 | 0.12 | 3 | 0.5 | 0.4 | 6 | 0.25 | 3 | 2.5 | >100 | 0.06 | 0.75 |
| Gram negative | | | | | | | | | | | | | | |
| Brucella melitensis A 488 | 12.5 | 12.5 | >100 | 0.75 | 100 | | | | 50 | 6 | 1.5 | >100 | 25 | 12.5 |
| Pasteurella multocida A 723 | 6 | 100 | >100 | 3 | 25 | 0.7 | 0.7 | 25 | 12.5 | 3 | 3 | >100 | 50 | 6 |
| Klebsiella pneumoniae A 809 | 25 | — | >100 | 3 | 100 | 0.7 | 12.5 | 25 | 100 | 3 | 6 | >100 | 50 | >100 |
| Salmonella duolin P 43 | 12.5 | 50 | >100 | 3 | >100 | 1.5 | 6 | 50 | >100 | 6 | 6 | >100 | >100 | >100 |
| Escherichia coli U 20 | 25 | >100 | >100 | 50 | >100 | 3 | 12.5 | 50 | >100 | 12.5 | 12.5 | >100 | >100 | >100 |
| Escherichia coli M D 165 | — | — | >100 | 50 | 100 | 3 | 6 | >50 | >100 | 6 | — | — | — | >100 |
| Shigella equir. T 3 | 12.5 | 12.5 | >100 | 6 | 100 | 1.5 | 1.5 | 50 | 100 | 1.5 | 1.5 | >100 | 50 | >100 |
| Pseudomonas aeroginosa H 10 | >100 | >100 | >100 | >100 | >100 | >50 | >50 | >50 | >100 | >100 | >100 | >100 | >100 | >100 |
| L 94 | | | >100 | >100 | >100 | >50 | >50 | >50 | >100 | >100 | >100 | — | — | >100 |
| Pseudomonas spec. 2396 | >100 | >100 | >100 | >100 | >100 | >50 | >50 | >50 | >100 | >100 | >100 | >100 | >100 | >100 |
| Pseudomonas aeroginosa Wyeth A 1058 | >100 | >100 | >100 | >100 | >100 | >50 | >50 | >50 | >100 | >100 | >100 | >100 | >100 | — |
| Proteus rettgeri A 821 | 3 | 25 | >100 | <12.5 | >100 | <12.5 | 0.6 | 12.5 | 50 | 12.5 | 12.5 | >100 | >100 | >100 |
| Proteus spec. H 3 | 25 | 100 | >100 | 25 | >100 | <12.5 | 1.5 | 50 | >100 | 25 | 12.5 | >100 | >100 | >100 |
| Proteus mirabilis L 93 | 12.5 | >100 | >100 | <12.5 | 50 | <12.5 | 0.3 | | | | | | | |
| Proteus spec. 2241 | >100 | >100 | >100 | >100 | >100 | >50 | >50 | | | | | | | |

-continued

| Strain of Bacteria. | H | I | J | K | L | M | N |
|---|---|---|---|---|---|---|---|
| mirabilis L 93 | 25 | >100 | 125 | 6 | >100 | 100 | >100 |
| Proteus spec. 2241 | >50 | >100 | >100 | >100 | >100 | >100 | >100 |

| Strain of Bacteria | O | P | Q | R | S | T |
|---|---|---|---|---|---|---|
| Gram positive | | | | | | |
| Bacillus subtilis ATCC 6633 | 1 | 50 | 0.12 | 3 | 1.5 | 6 |
| Staphylococcus aureus | | | | | | |
| A 55 | — | — | — | — | — | — |
| A 321 | 1.5 | 25 | 12.5 | 12.5 | 3 | 25 |
| A 355') | 1.5 | 50 | 25 | 50 | 12.5 | 25 |
| L 160a') | — | — | — | — | 12.5 | 25 |
| Streptococcus haemolyticus A 266 | 0.06 | 1.5 | 0.12 | 1.5 | 12.5 | 1.5 |
| Streptococcus faecalis L 80 | 50 | >100 | 25 | 100 | 25 | >100 |
| Diplococcus pneumoniae L 54 | 1.5 | 100 | 0.5 | 6 | 0.5 | 12.5 |
| Gram negative | | | | | | |
| Brucella melitensis A 488 | 100 | >100 | 12.5 | 25 | 100 | 25 |
| Pasteurella multocida A 723 | 25 | >100 | 6 | 25 | 25 | 100 |
| Klebsiella pneumoniae A 809 | 100 | >100 | 100 | >100 | >100 | >100 |
| Salmonella dublin P 43 | >100 | >100 | 6 | >100 | >100 | >100 |
| Escherichia coli U 20 | >100 | >100 | 25 | >100 | >100 | >100 |
| Escherichia coli M D 165 | — | — | — | — | — | — |
| Shigella equir. T 3 | — | — | 6 | 50 | >100 | >100 |
| Pseudomonas aeruginosa H 10 | >100 | >100 | >100 | >100 | >100 | >100 |
| L 94 | — | — | — | — | — | — |
| Pseudomonas spec. 2396 | >100 | >100 | >100 | >100 | >100 | >100 |
| Pseudomonas aeruginosa Wyeth A 1058 | >100 | >100 | >100 | >100 | >100 | >100 |
| Proteus rettgeri A 821 | >100 | >100 | 1.5 | 100 | 25 | >100 |
| Proteus spec. H 3 | >100 | >100 | 50 | >100 | 100 | >100 |
| Proteus mirabilis L 93 | >100 | >100 | 6 | 50 | 2 | >100 |
| Proteus spec. 2241 | >100 | >100 | >100 | >100 | >100 | >100 |

Table I shows that the R-sulfoxides of the invention, viz. compounds D, G, K, O, Q and S possess substantially better antibacterial activity than the corresponding S-sulfoxides (compounds C, H, L, P, R and T). Moreover, sulfoxide compounds D and G possess greater antibacterial properties than the corresponding unoxided compounds E and F. Compound I shows particularly high gram-positive antibacterial activity.

Various modifications of the process and compositions of the invention may be made without departing from the spirit or scope thereof and it should be understood that the invention is to be limited only as defined in the appended claims.

We claim:

1. A method of combatting bacterial infections in warm-blooded animals comprising administering to said warm-blooded animals a bactericidally effective amount of a compound selected from the group consisting of 7-phenylacetamido-$\Delta^3$-desacetoxycephalosporanic acid R-sulfoxide and non-toxic, pharmaceutically acceptable salt thereof.

2. A method of combatting bacterial infections in warm-blooded animals comprising administering to said warm-blooded animal a bactericidally effective amount of a compound selected from the group consisting of 7-$\alpha$-amino-phenylacetamido-$\Delta^3$-desacetoxycephalosporanic acid R-sulfoxide and non-toxic, pharmaceutically acceptable salt thereof.

* * * * *